US006781681B2

(12) United States Patent
Horwitz

(10) Patent No.: US 6,781,681 B2
(45) Date of Patent: Aug. 24, 2004

(54) SYSTEM AND METHOD FOR WAVEFRONT MEASUREMENT

(75) Inventor: Larry S. Horwitz, Seal Beach, CA (US)

(73) Assignee: Ophthonix, Inc., San Diego, CA (US)

( * ) Notice: Subject to any disclaimer, the term of this patent is extended or adjusted under 35 U.S.C. 154(b) by 0 days.

(21) Appl. No.: 10/014,037

(22) Filed: Dec. 10, 2001

(65) Prior Publication Data

US 2003/0231298 A1 Dec. 18, 2003

(51) Int. Cl.[7] ............................................. G01M 11/00
(52) U.S. Cl. ................................................... 356/124.5
(58) Field of Search ................................ 356/124–127

(56) References Cited

U.S. PATENT DOCUMENTS

| | | |
|---|---|---|
| 4,711,576 A | 12/1987 | Ban |
| 5,062,702 A | 11/1991 | Bille |
| 5,080,477 A | 1/1992 | Adachi |
| 5,164,750 A | 11/1992 | Adachi |
| 5,528,321 A | 6/1996 | Blum et al. |
| 5,777,719 A | 7/1998 | Williams et al. |
| 5,949,521 A | 9/1999 | Williams et al. |
| 5,963,300 A | 10/1999 | Horwitz |
| 6,007,204 A | 12/1999 | Fahrenkrug et al. |
| 6,050,687 A | 4/2000 | Bille et al. |

(List continued on next page.)

FOREIGN PATENT DOCUMENTS

| | | |
|---|---|---|
| WO | WO 92/01417 | 2/1992 |
| WO | WO 98/27863 | 7/1998 |
| WO | WO 00/19885 | 4/2000 |
| WO | WO 01/47449 | 7/2001 |
| WO | WO 01/82791 | 11/2001 |
| WO | WO 01/89424 | 11/2001 |
| WO | WO 02/09579 | 2/2002 |
| WO | WO 02/19901 | 3/2002 |
| WO | WO 02/28272 | 4/2002 |
| WO | WO 02/30273 | 4/2002 |
| WO | WO 03/009746 A1 | 6/2003 |

OTHER PUBLICATIONS

Hiroshi Ohba, *Wavefront Sensor Using a 2–Dimensional Diffraction Grating*, Japanese Journal of Applied Physics, vol. 37, 1998, pp. 3749–3753.

Patrick P. Naulleau et al., *Extreme ultraviolet carrier–frequency shearing interferometry of a lithographic four–mirror optical system*, J. Vac. Sci. Technol. B, vol. 18, No. 6, Nov./Dec. 2000, pp. 2939–2943.

Helen L. Kung, *Micro–optical wavelength detectors*, http://clynlish.stanford.edu/~hlkung/research.html, printed Jun. 9, 2003, 3 pages.

SPIEWeb Scholarly Journals, *Optical Engineering*, vol. 38, No. 12, Dec. 1999, http://www.sple.org/web/journals/oe/oedec99.html, printed Jun. 9, 2003, 8 pages.

*Primary Examiner*—Frank G. Font
*Assistant Examiner*—Amanda Merlino
(74) *Attorney, Agent, or Firm*—Knobbe Martens Olson & Bear LLP

(57) ABSTRACT

A wavefront measuring system and method for detecting phase aberrations in wavefronts that are reflected from, transmitted through or internally reflected within objects sought to be measured, e.g., optics systems, the human eye, etc. includes placing a reticle in the path of a return beam from the object, and placing a detector at a diffraction pattern self-imaging plane relative to the reticle. The diffraction pattern is analyzed and results in a model of the wavefront phase characteristics. A set of known polynomials is fitted to the wavefront phase gradient to obtain polynomial coefficients that describe aberrations in the object or within the wavefront source being measured.

24 Claims, 3 Drawing Sheets

U.S. PATENT DOCUMENTS

| | | |
|---|---|---|
| 6,086,204 A | 7/2000 | Magnante |
| 6,095,651 A | 8/2000 | Williams et al. |
| 6,112,114 A | 8/2000 | Dreher |
| 6,120,150 A | 9/2000 | Sarver et al. |
| 6,155,684 A | 12/2000 | Bille et al. |
| 6,199,986 B1 | 3/2001 | Williams et al. |
| 6,234,631 B1 | 5/2001 | Sarver et al. |
| 6,256,098 B1 | 7/2001 | Rubinstein et al. |
| 6,257,723 B1 | 7/2001 | Sarver et al. |
| 6,270,221 B1 | 8/2001 | Liang et al. |
| 6,271,915 B1 | 8/2001 | Frey et al. |
| 6,299,311 B1 | 10/2001 | Williams et al. |
| 6,305,802 B1 | 10/2001 | Roffman et al. |
| 6,338,559 B1 | 1/2002 | Williams et al. |
| 6,379,005 B1 | 4/2002 | Williams et al. |
| 6,379,008 B1 | 4/2002 | Chateau et al. |
| 6,382,795 B1 | 5/2002 | Lai |
| 6,394,605 B1 | 5/2002 | Campin et al. |
| 6,396,588 B1 | 5/2002 | Sei |
| 6,499,843 B1 | 12/2002 | Cox et al. |
| 2001/0033362 A1 | 10/2001 | Sarver |
| 2001/0035939 A1 | 11/2001 | Mihashi et al. |
| 2001/0041884 A1 | 11/2001 | Frey et al. |
| 2002/0047992 A1 | 4/2002 | Graves et al. |
| 2002/0140902 A1 | 10/2002 | Guirao et al. |
| 2002/0167643 A1 | 11/2002 | Youssefi |
| 2002/0186346 A1 | 12/2002 | Stantz et al. |
| 2002/0196412 A1 | 12/2002 | Abitbol |
| 2003/0011745 A1 | 1/2003 | Molebny et al. |

SYSTEM AND METHOD FOR WAVEFRONT MEASUREMENT

FIELD OF THE INVENTION

The present invention relates generally to systems and methods for measuring phase characteristics of electromagnetic wavefronts.

BACKGROUND

Measuring how a wavefront deviates from perfectly diffraction-limited has many applications. As non-limiting examples, measuring deviations, also referred to as "aberrations", in a wavefront produced by an optical system, such as a telescope, can reveal manufacturing flaws in the system, since many optical systems, to function as best as is possible, must produce perfectly diffraction-limited wavefronts. By adding a component to the system that produces a wavefront that is the conjugate of the measured deviations, the system can be made to produce a more diffraction-limited wavefront and, thus, diffraction-limited performance (i.e., best possible performance).

Another example of an application where knowing the aberrations in a wavefront is useful is in correcting human vision. For instance, as noted in U.S. Pat. No. 5,963,300, by measuring deviations from the perfectly spherical in reflections of laser light from the eye of a patient, aberrations of the eye can be measured and, hence, compensated for. In the '300 patent, light that is reflected from a patient's eye is passed through two reticles, and the resulting moiré shadow pattern is presented on a screen. An imaging system images the shadow on the screen onto a camera, with subsequent analysis being undertaken of the imaged shadow. The technique of the '300 patent is based on geometrical or ray-tracing analysis, which as recognized herein requires theoretical assumptions to perform the geometrical analysis that limit the amplitude of the aberrations that can be measured as well as limit the accuracy with which the aberrations can be measured.

With these drawbacks in mind, the present invention provides the solutions below to one or more of them.

SUMMARY OF THE INVENTION

A system for determining aberrations in a coherent electromagnetic wavefront includes a reticle that is positioned in the path of the wavefront, and a detector is also positioned in the path. In accordance with this aspect, the light detector is located at a diffraction pattern self-imaging plane relative to the reticle.

A processor receives the output signal from the light detector and determines aberrations in the beam based thereon. The aberrations in the beam represent aberrations in the wavefront due to the medium through which it passes, or an object from which it reflects, or the source of the wavefront itself.

In a preferred, non-limiting embodiment, the processor executes logic that includes determining a phase gradient of the wavefront phase-front, and determining coefficients of polynomials based on the phase-front gradient which quantify the aberrations. The coefficients represent aberrations. Preferably, the gradient is obtained from a frequency domain transformation of the beam, such that the gradient is the derivatives of phases of the wavefront in directions established by the reticle orientation. In a particularly preferred, non-limiting embodiment, the derivatives are determined in at least two directions, and the coefficients are determined by fitting derivatives of a set of known polynomials to the measured gradient.

In another aspect, a method for determining aberrations in an object includes passing a light beam from the object through a reticle, and then determining derivatives that are associated with the light beam subsequent to the light beam passing through the reticle. Using the derivatives, a measure of aberrations in the object can be output.

In yet another aspect, a computer program product includes a computer readable medium having a program of instructions stored thereon for causing a digital processing apparatus to execute method steps for determining aberrations in an object. The product includes means for receiving a representation of a wavefront propagating into the apparatus, and means for determining wavefront aberrations of the representation. Means are provided for fitting the derivatives to known polynomials or derivatives thereof to obtain coefficients of polynomials. The product includes means for outputting a wavefront characterization based at least in part on the coefficients, with the signal representing aberrations in the object.

In still another aspect, an apparatus for detecting aberrations in an object as manifested in a wavefront includes a reticle positioned in a path of the wavefront and a light detector positioned relative to the reticle to receive the diffracted self-image that is associated with the wavefront. The self-imaging distances are at discrete distances from the reticle that are integral multiples of, where p is the period of the reticle and the λ is the spectral wavelength of the wavefront. A processor receives signals from the light detector that represent the self-image. The processor derives the wavefront phase gradient associated with the wavefront and uses the coefficients of derivatives of polynomials that define the wavefront to determine the wavefront aberrations.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

Figure 1:
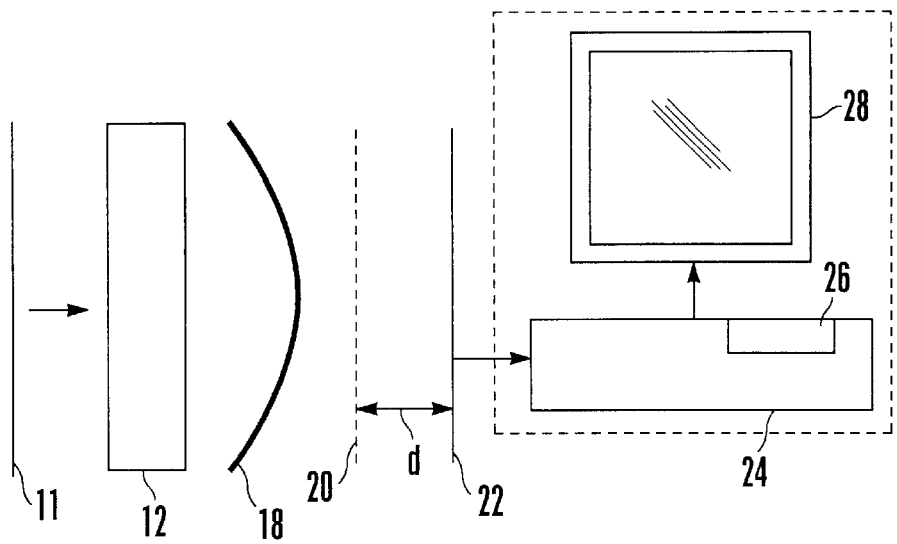
FIG. 1 is a block diagram of the present system architecture.

Referring initially to FIG. 1, a wavefront sensor is shown, generally designated 10. As shown in FIG. 1, a reference wavefront 11 can pass through (or, be reflected from) a transfer (optical or otherwise) system or element 12. The system or element 12 can be an optics system, such as a telescope system, or it can be a human eye, or other object having aberrations sought to be measured.

As shown in FIG. 1, a transferred wavefront 18, i.e., the wavefront 11 after having passed through or having been reflected from the system or element 12, passes through a reticle 20. The reticle 20 diffracts the wavefront 18, and the diffracted wavefront self-images onto a sensor plane a self-imaging distance "d" away from the reticle 20, at which location is disposed a light sensor 22 such as but not limited to a CCD. The self-imaging distance "d" is dependent on the spectral wavelength of the coherent wavefront and the spatial frequency of the reticle.

In a non-limiting, exemplary embodiment, the wavefront incident on the imaging detector can be represented by the following diffraction equation:

$$I(\vec{r}, z) = I_o \cos\left(\frac{\pi \lambda z}{p^2}\right) \cos\left[\frac{2\pi}{p}\left(\vec{r} \cdot \hat{p} - \hat{r} \cdot \left(\hat{z} X \vec{\nabla} w\right)\right)\right] \quad (1)$$

wherein λ is the wavelength of the coherent wavefront, z is the propagation distance, p is the period of the reticle (distance from the beginning of one grid line to the next grid line), r is the spatial dimension in the plane of the detector with its associated vector, r̂ is the unit vector, p̂ the unit vector representing the reticle orientation, and ∇ is the directional—derivative (or, gradient) of the wavefront phase "w" that is being measured. The self-imaging distance is dependent on the spectral wavelength of the coherent wavefront and the spatial frequency of the reticle is given by:

$$d = \left(\frac{np^2}{\lambda}\right) \quad (2)$$

where n is the integer multiple at which distances the self-images occurs.

Accordingly, the self-imaged reticle on the light sensor or detector 22 that is located at the self-image plane contains the desired information pertaining to the phase characteristics of the coherent wavefront. This information is extracted from the spatial signal collected at the sensor 22 and sent to a data processor (i.e., computer) 24 for processing in accordance with the disclosure below. To undertake the present logic, the processor 24 accesses a preferably software-implemented module 26, and outputs a signal representative of the wavefront (or a conjugate thereof) to an output device 28, such as but not limited to a printer, monitor, computer, network, or other appropriate output device.

In accordance with present principles, the beam that emerges from the reticle 20 establishes a diffraction pattern. This pattern, however, substantially cannot be discerned except at the self-image planes that are spaced integer multiples of a distance "d" from the reticle 20, as discussed above. Thus, the self image of the diffusion pattern can be detected by the light sensor or detector 22 that in one preferred embodiment is placed at the first (n=1) self-image plane as shown in FIG. 1, although it is to be understood that the sensor or detector 22 can be positioned at any of the self-image planes that are spaced from the reticle 20 by integer multiples of the distance "d".

Figure 2:
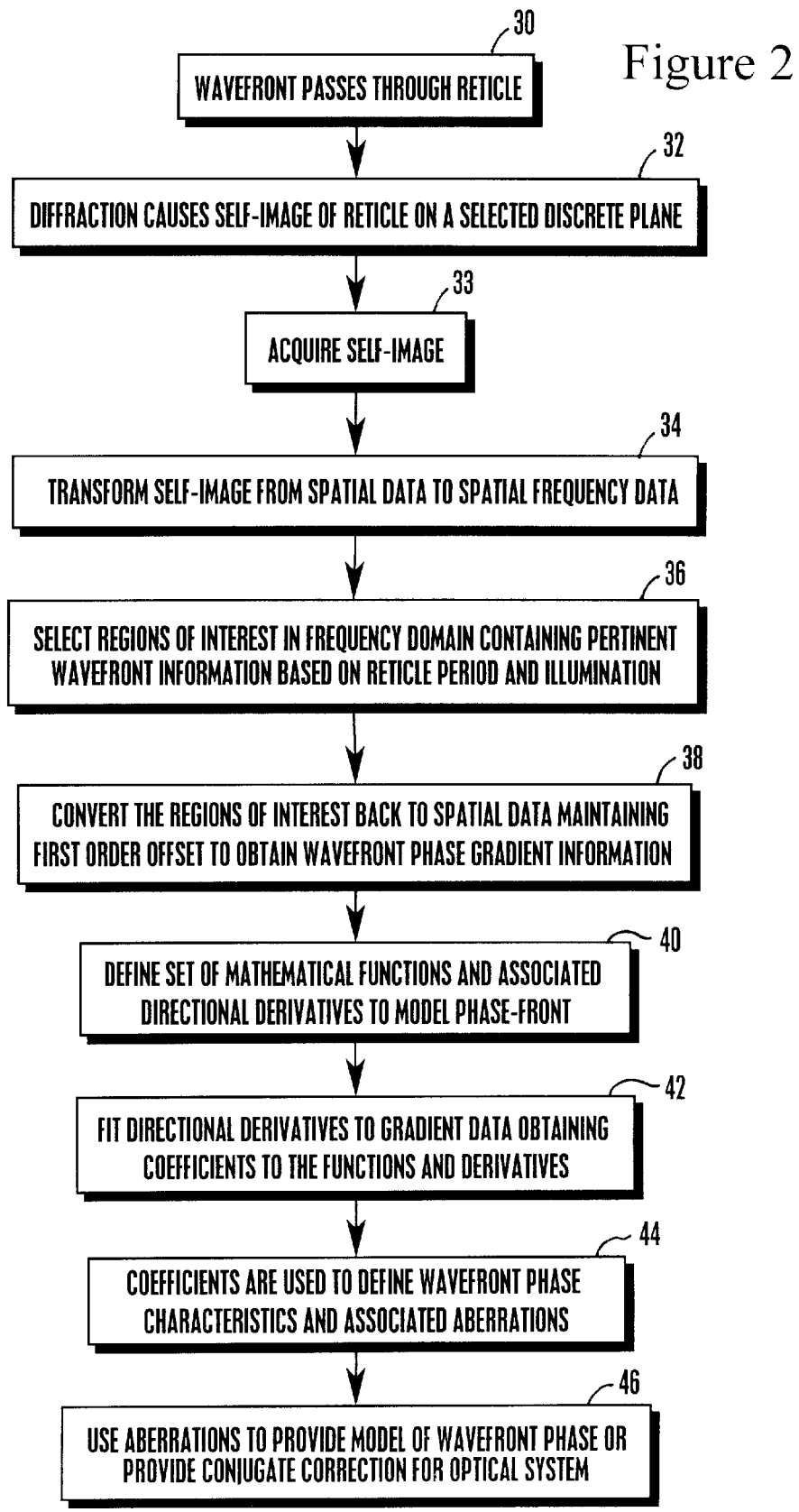
FIG. 2 is a flow chart of the overall logic of the invention.

It is to be understood that the present logic is executed on the architecture shown in FIG. 1 in accordance with some or all of the blocks in the flow chart of FIG. 2, which illustrates the structure of the logic of the present invention as embodied in computer program software. Those skilled in the art will appreciate that the flow charts illustrate the structures of logic elements, such as computer program code elements or electronic logic circuits, that function according to this invention. Manifestly, the invention is practiced in its essential embodiment by a machine component that renders the logic elements in a form that instructs a digital processing apparatus (that is, a computer, controller, processor, etc.) to perform a sequence of function steps corresponding to those shown.

In other words, the logic may be embodied by a computer program that is executed by the processor 24 as a series of computer- or control element-executable instructions. These instructions may reside, for example, in RAM or on a hard drive or optical drive, or the instructions may be stored on magnetic tape, electronic read-only memory, or other appropriate data storage device that can be dynamically changed or updated.

Figure 1A:
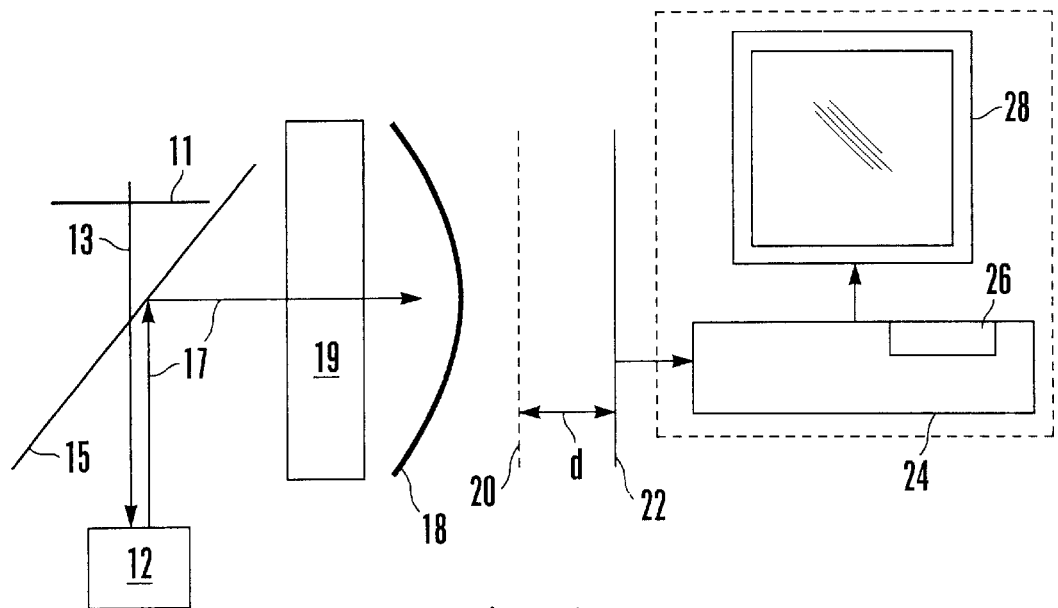
FIG. 1a is a block diagram of a more detailed implementation of the system shown in FIG. 1.

FIG. 1a shows a particular non-limiting implementation of the system 10 in which the electromagnetic energy is reflected from an object or is internally reflected from within an object. Examples of applications include microwave topography of large surfaces, wherein the electromagnetic energy is microwave and the object is the surface sought to be measured; optical topography of reflective surfaces, wherein the electromagnetic energy is laser light; retinal reflection within an eye in order to measure the aberrations of the eye, and gamma ray reflection within very small objects in order to characterize mechanical or optical properties.

Accordingly, for illustration purposes FIG. 1a shows that the reference wavefront 11 passes through (or, is reflected from) a transfer (optical or otherwise) system or element 15, such as but not limited to a beamsplitter, along a propagation path 13. The wavefront 11 is incident on an object 12 such as a human eye wherein it is either reflected externally or transmits into the object 12 where it is internally reflected. The return wavefront follows along a return path 17, and can be reflected from or transmitted through the system or element 15. The wavefront may then pass through an optical relay system 19. The transferred wavefront 18 passes through the reticle 20 and is processed as described above in reference to FIG. 1.

The logic of the processor 24 can be appreciated in reference to FIG. 2. Commencing at block 30 in FIG. 2, the wavefront 18 of the beam passes through the reticle 20. Diffraction effects cause a self-image of the reticle to appear at the self-image planes described above, including at the first plane located at a distance "d" from the reticle 20 where the detector 22 is positioned. The particular plane chosen for the position of the detector 22 should have sufficient resolution cells to resolve the diffraction pattern.

The self-image of the diffraction pattern caused by the beam 18 passing through the reticle 20 is acquired at block 33 by the sensor or detector 22 and is represented by the signal output by the light detector 22, as received by the processor 24. Proceeding to block 34, the signal in the spatial image domain is transformed to the spatial frequency domain. In one non-limiting embodiment, executing a Fast Fourier Transform (FFT) on the signal performs this, although it is to be understood that other mathematical transformations can be used. While FIG. 2 indicates that the FFT is implemented in software, it is to be understood by those skilled in the art that alternatively, prior to being sent to the processor 24 an optical FFT of the return beam can be made using optics known in the art.

Proceeding to block 36, regions of interest in the frequency domain are selected based on reticle period and other factors discussed further below. This selection can be a priori, and need not be undertaken during measurement. Essentially, at block 36 the regions of interest for which gradient (directional derivative) of the wavefront is to be determined are located in the spatial frequency domain and isolated.

In the preferred embodiment, the portions of the spatial frequency domain that contain the slope information and that consequently are isolated depend on the configuration of the reticle 22 and can be, e.g., represented by orthogonal axes of the FFT. This spatial frequency domain manipulation is further illustrated in FIG. 3, discussed below.

Proceeding to block 38, an inverse transform is applied only to the isolated regions of the signal to render a spatial representation of the gradient of the wavefront in the direction normal to the linear or segmented linear dimension of the reticle. Thus, if the reticle contains a singular set of linear grating lines, there will be two regions of the spatial frequency domain containing the desired information. If there are two sets of linear gratings superimposed in the reticle, the spatial frequency domain will contain four regions of interest. Each additional set of linear gratings provides more information pertaining to the wavefront gradient. In the limit, a circular grating reticle represents an infinite number of segmented linear gratings superimposed on each other. Preferably, the reticle contains two orthogonal superimposed linear grating patterns. In a non-limiting preferred embodiment, the wavefront gradient is determined in isolated regions in two directions. In a non-limiting example, when the object 12 is a human eye, the two directions are orthogonal to each other and lie in a plane defined by the front of and tangential to the patient's eye, with one of the directions extending from the center of the eye at a 45° angle relative to the horizontal and tangent to the eye when the patient is standing and facing directly forward.

If desired, in a non-limiting embodiment filtering of random background noise can be further effected by using a "computationally-implemented" matte screen by which the spatial characteristics of the self-image are enhanced and the background reduced to very low (i.e., zero) frequency components in the spatial frequency domain. This principle will be further discussed in relation to FIG. 4.

Moving to block 40, a set of known functions such as polynomials (and their derivatives) is defined or otherwise accessed for the two directions mentioned above. These polynomials can be used to model the wavefront. In one preferred, non-limiting embodiment, a set of 36 Zernike polynomials are used. Then, at block 42 the derivatives of the known polynomials are fit to the derivatives (i.e., gradient) determined at block 38 using, e.g., a least squares fit or other fitting algorithm.

The outcome of the fitting step at block 42 is that each polynomial has an accompanying coefficient, also referred to as the "amplitude" of the polynomial. Each coefficient represents an aberration from the perfectly spherical in the return beam 18 and, hence, an aberration in the object 12. Consequently, at block 44 a reconstructed wavefront equation can be output (to, e.g., the output device 28) that is the set of the known polynomials with the coefficients obtained in the fitting step at block 42. At block 46, the output, and in particular the coefficients in the reconstructed wavefront equation, can be used to indicate aberrations in the original wavefront and, hence, in the object 12. Furthermore, the output can be used as a basis for implementing corrective optics for the system 12 that essentially represent the conjugate of the polynomials and/or coefficients to null out the aberrations of the object 12.

Figure 3:
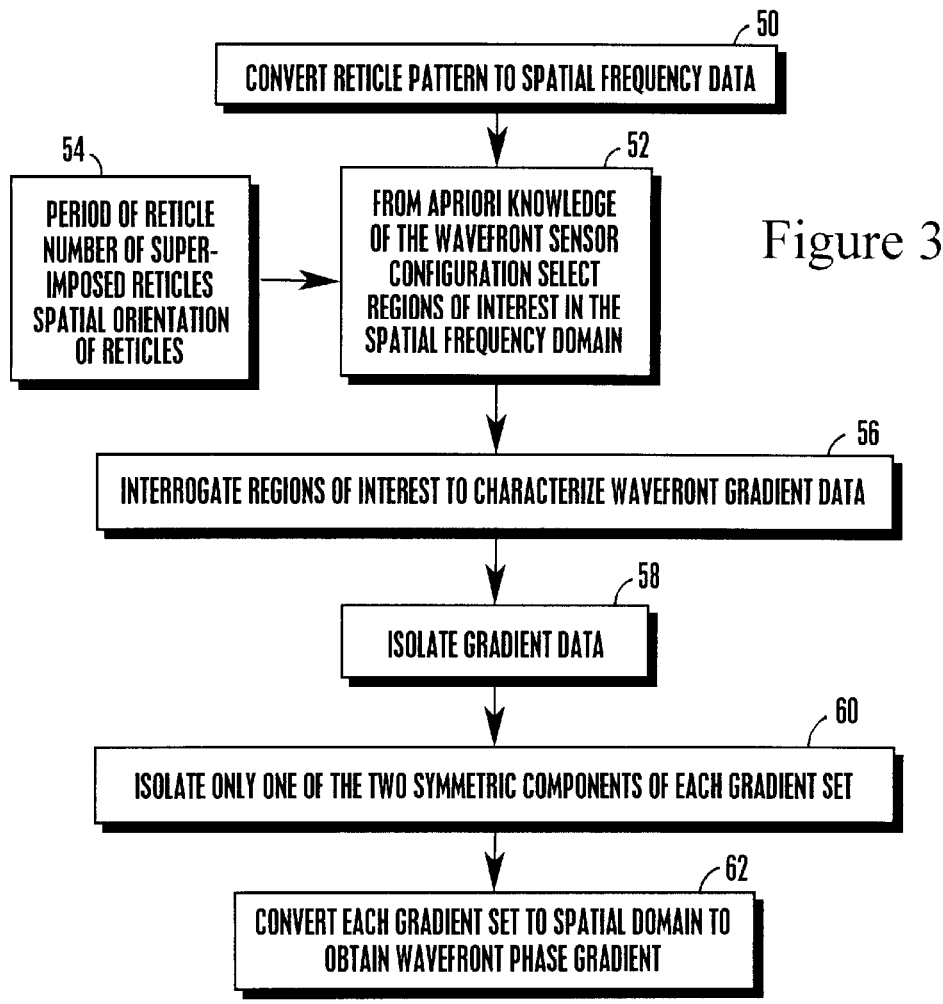
FIG. 3 is a flow chart of the logic for data extraction in the spatial frequency domain.

Now referring to FIG. 3, which shows further details of blocks 34, 36 and 38 in FIG. 2, at block 50 the self-image of the reticle is converted in software or optically from spatial data to spatial frequency data. As discussed above, this is preferably performed with a Fourier Transform algorithm and preferably the Fast Fourier Transform computer software algorithm (FFT). Moving to block 52, from an a priori knowledge of the system 10 configuration, regions of interest in the spatial frequency domain are selected. The a priori information is provided at block 54 as follows. The reticle 20 has (a) periodic pattern(s) in known directions. The period of the reticle, the number of superimposed reticles, and the spatial orientations of the reticle relative to the wavefront path of propagation are needed to locate these regions. Gradiant data in the individual regions of interest is accessed at block 56 and isolated at block 58. This data has symmetry in the spatial frequency domain. Accordingly, in block 60 if desired only one of the symmetric data sets need be selected. Then in block 62 each set is converted back to the spatial domain. This data is then passed to block 38 in FIG. 2.

The above operations by which the wave front is extracted from equation (1) can be expressed in analytical form as follows. First, the non-limiting Fourier transform on the wavefront executed at block 50 in FIG. 3 can be expressed as $$F\{I(r,z)\}\begin{matrix}fx, y2 & fx, y4\\ fx, y1' & fx, y3\end{matrix} \Rightarrow F(\sigma w). \tag{3}$$

Wherein the two spatial frequency regions $f_{x,y1}$ to $f_{x,y2}$ and $f_{x,y3}$ to $f_{x,y4}$ are the two dimensional areas in the frequency domain that contain the relevant data, and F ($\sigma$w) represents the received wavefront.

Then, the gradient ($\sigma$w) of the wavefront is determined at block 56 by performing the inverse Fourier transform ($F^{-1}$) on equation (3) as follows:

$$F^{-1}\{F(\sigma w).\} \rightarrow \sigma w. \tag{4}$$

Next, the set of partial derivatives, or gradients, of the chosen polynomial set, e.g., Zernike polynomials ($\sigma$Z, or $Z_x$ and $Z_y$) are made to best approximate the gradient of the phase front ($\sigma$w) at block 42 of FIG. 2 via any algorithm such as a least squares algorithm which is well know in the art. That is, $$\sigma w = \sum_{i=1}^{n} A_i \sigma Z_i, \tag{5}$$

wherein n is the number of polynomials chosen to best approximate the wavefront phase gradient, and $A_i$ is the coefficient, or amplitude, of the polynomial $Z_i$. The wavefront phase "w" can now be described as follows:

$$w = \sum_{i=1}^{n} A_i Z_i. \tag{6}$$

The aberrations in the wavefront can be described by the values of the coefficients Ai.

Figure 4:
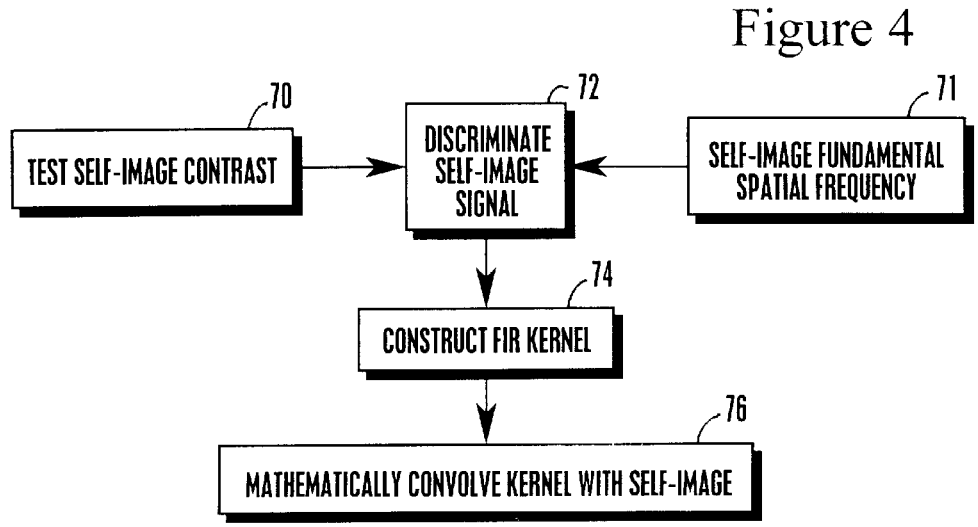
FIG. 4 is a flow chart of further logic for extraction of the desired data from spatial frequency data.

The flow chart of FIG. 4 shows the process of the "computationally-implemented" matte screen discussed above in relation to FIG. 2. Typically, in a monochromatic system a high pass spectral filter is used to eliminate signal noise. This is a piece of hardware called a matte screen. In many applications a matte screen is not practical to integrate into the system. Accordingly, the matte screen can be computationally implemented on the self-images.

The contrast of the image and the self-image fundamental spatial frequency are respectively received from blocks 70 and 71 and input to block 72, where the two inputs are compared to discriminate the self-image signal. If the contrast from block 70 is lower than the fundamental spatial frequency from block 71, the matte screen is implemented within block 34 of FIG. 2, with the location of the peak value in the region of interest in block 38 providing the fundamental (predominant) frequency within the self-image signal. From the peak, a finite impulse response (FIR) kernel is derived at block 74 that functions as a high-pass filter of spatial frequency data. Only frequencies higher then the designed limit will remain in the signal, and all others are eliminated at block 76 by mathematically convolving the kernal with the self-image signal.

While the particular SYSTEM AND METHOD FOR WAVEFRONT MEASUREMENT as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more". All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. §112, sixth paragraph, unless the element is expressly recited using the phrase "means for" or, in the case of a method claim, the element is recited as a "step" instead of an "act".

What is claimed is:

1. A system for determining aberrations in an electromagnetic wavefront, comprising:
   at least one source of the electromagnetic wavefront directing a beam onto an object system, the object system reflecting or passing at least part of the beam to render a wavefront to be analyzed;
   at least one reticle positioned in a path of the wavefront to be analyzed;
   at least one detector positioned to detect the wavefront passing through the reticle, the detector being located at a diffraction pattern self-imaging plane relative to the reticle; and
   at least one processor receiving an output signal from the light detector and determining at least one aberration in the wavefront based thereon, the aberration representing at least one aberration in the object system,
   wherein the processor executes logic to undertake method acts comprising:
   accessing mathematical functions to characterize the electromagnetic wavefront; and
   determining directional derivatives of the electromagnetic wavefront using the mathematical functions.

2. The system of claim 1, wherein the method acts include determining coefficients of polynomials based on at least one gradient of a phase-front of the wavefront, the coefficients being representative of aberrations.

3. The system of claim 2, wherein the method acts further include transforming the wavefront from a spatial image domain into a spatial frequency domain, prior to the act of determining coefficients.

4. The system of claim 3, wherein only selected portions in the spatial frequency domain are used to determine coefficients.

5. The system of claim 3, wherein the act of determining coefficients includes determining directional-derivatives of phases of the wavefront.

6. The system of claim 5, wherein directional derivatives are determined in at least two directions.

7. The system of claim 6, wherein the coefficients are determined by fitting derivative functions of a set of known polynomials to the derivatives obtained during the determining act.

8. A method for determining aberrations in an object system, comprising:
   passing a light beam from the object system through a reticle;
   transforming a wavefront associated with the light beam from a spatial image domain into a spatial frequency domain;
   determining directional derivatives associated with the light beam subsequent to the light beam passing through the reticle; and
   determining coefficients of polynomials based on the directional derivatives,
   wherein the derivatives are used to output a measure of aberrations in the light beam.

9. The method of claim 8, wherein the act of determining derivatives includes determining derivatives of phases of the wavefront.

10. The method of claim 9, comprising determining directional derivatives in at lest two directions.

11. The method of claim 10, wherein the coefficients are determined by fitting derivatives of a set of known polynomials to data obtained during the determining act.

12. An apparatus for detecting aberrations in an object system as manifested in a wavefront from the object system, comprising:
   at least one reticle positioned in a path of the wavefront;
   at least one light detector positioned relative to the reticle to receive a self-image of at least one diffraction-caused pattern associated with the wavefront; and
   at least one processor receiving signals from the light detector representative of the self-image and deriving derivatives associated therewith, the processor using the derivatives to determine the aberrations,
   wherein the processor receives a frequency transformation of the wavefront and derives derivatives associated with phases of the frequency transformation, the processor determining derivatives of phases in two directions.

13. The apparatus of claim 12, wherein the processor fits a set of known derivatives to the derivatives determined by the processor to obtain coefficients of polynomials representative of the aberrations.

14. The apparatus of claim 13, wherein only selected portions in a spatial frequency domain are used to determine coefficients.

15. A computer program product, comprising:
   a computer readable medium having a program of instructions stored thereon for causing a digital processing apparatus to execute method steps for determining aberrations in at least one object, comprising:

means for receiving at least one representation of a wavefront propagating from the object;

means for determining directional derivatives of the representation;

means for fitting the directional derivatives to known polynomials or derivatives thereof to obtain coefficients of polynomials; and means for outputting at least one signal based at least in part on the coefficients, the signal representing aberrations in the object.

16. The program product of claim 15, further comprising:

means for generating a frequency domain representation of the wavefront.

17. The program product of claim 16, wherein the means for determining determines derivatives of phases in two directions.

18. A method for determining aberrations in a reflective or internally reflective object, comprising;

passing a light beam from the object through a reticle;

determining directional derivatives associated with the light beam subsequent to the light beam passing through the reticle; and using the derivatives to output a measure of aberrations in the light beam and, hence, the object.

19. The method of claim 18, wherein the object is an eye of a patient.

20. The method of claim 19, further comprising transforming a wavefront associated with the light beam from a spatial image domain into a spatial frequency domain.

21. The method of claim 20, further comprising determining coefficients of polynomials based on the direction derivatives.

22. The method of claim 21, wherein the act of determining derivatives includes determining derivatives of phases of the wavefront.

23. The method of claim 22, comprising determining directional derivatives in at least two directions.

24. The method of claim 23, wherein the coefficients are determined by fitting derivatives of a set of known polynomials to data obtained during the determining act.

* * * * *